United States Patent
Schubart et al.

(10) Patent No.: US 6,534,675 B2
(45) Date of Patent: Mar. 18, 2003

(54) PROCESS FOR THE PREPARATION OF ZINC DITHIOCARBAMATES

(75) Inventors: Rüdiger Schubart, Gladbach (DE); Hans-Wilhelm Engels, Kerpen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/824,078

(22) Filed: Apr. 2, 2001

(65) Prior Publication Data
US 2001/0039339 A1 Nov. 8, 2001

(30) Foreign Application Priority Data
Apr. 6, 2000 (DE) .......................................... 100 17 103

(51) Int. Cl.⁷ ............................................. C07C 327/00
(52) U.S. Cl. ........................................... 562/28; 562/27
(58) Field of Search ................................ 562/556, 555, 562/27, 28; 556/134; 260/665

(56) References Cited

U.S. PATENT DOCUMENTS

| | | | | | |
|---|---|---|---|---|---|
| 2,229,652 A | * | 1/1941 | Gracia | ...................... | 585/606 |
| 2,388,468 A | * | 11/1945 | Compton | ..................... | 556/134 |
| 3,067,090 A | * | 12/1962 | Groningen | ................ | 514/237.5 |
| 3,133,947 A | * | 5/1964 | Cerrito | | |
| 3,151,119 A | * | 9/1964 | Grisley et al. | ............... | 546/245 |
| 3,167,571 A | * | 1/1965 | D'Amico et al. | ........... | 558/232 |
| 3,954,729 A | * | 5/1976 | Sato et al. | ................... | 540/608 |
| 4,079,146 A | * | 3/1978 | Miller et al. | ................ | 514/481 |
| 4,185,113 A | * | 1/1980 | Virrion et al. | .............. | 514/483 |
| 4,831,171 A | * | 5/1989 | Bergfeld et al. | ............ | 556/134 |

FOREIGN PATENT DOCUMENTS

| | | | |
|---|---|---|---|
| DE | 4102337 | * | 7/1992 |
| IN | 149456 | * | 12/1981 |

* cited by examiner

Primary Examiner—Jean F. Vollano
(74) Attorney, Agent, or Firm—Joseph C. Gil; Noland J. Cheung; Jennifer R. Seng

(57) ABSTRACT

Zinc dithiocarbamates are obtained in especially readily filterable form and high purity when zinc salts are first added, in aqueous solution, to the secondary amines underlying the zinc carbamates, so that a zinc salt complex of the amines is formed, and carbon disulfide and then sodium hydroxide solution are then introduced, with stirring, into the aqueous suspension so obtained, the temperatures being maintained in the range from room temperature to the boiling temperature of carbon disulfide until the reaction has completely finished.

3 Claims, No Drawings

PROCESS FOR THE PREPARATION OF ZINC DITHIOCARBAMATES

FIELD OF THE INVENTION

The invention relates to a process for the preparation of zinc dithiocarbamates, wherein the zinc dithiocarbamates are obtained in especially readily filterable form and high purity.

BACKGROUND OF THE INVENTION

The preparation of zinc dithiocarbamates, which are used primarily in plant protection as fungicides and in the rubber industry as vulcanization accelerators for natural and synthetic rubbers, is conventionally carried out by reacting secondary amines with carbon disulfide in the presence of ammonia or lye to form the corresponding dithiocarbamates, which are then converted by means of zinc salts into the sparingly soluble zinc dithiocarbamates.

A further possible method of preparing zinc dithiocarbamates is the reaction of secondary amines in the presence of zinc oxide and carbon disulfide.

A disadvantage of the known processes for the preparation of zinc dithiocarbamates is especially that the zinc dithiocarbamates obtained are of small particle size and irregular particle-size distribution, and accordingly, are difficult to filter. Since the particle sizes obtained are greatly dependent on the particular precipitation temperature of the zinc dithiocarbamates from the reaction mixture—a larger particle size at a higher precipitation temperature—one possible method of obtaining larger particle sizes would be to raise the precipitation temperature. That possibility is limited, however, by the fact that the carbon disulfide used has a low boiling point and therefore, is readily volatile. Furthermore, carbon disulfide is readily combustible. For that reason, precipitation of zinc dithiocarbamates at a higher temperature is problematic.

SUMMARY OF THE INVENTION

The object of the present invention is to provide a simple process for the preparation of zinc dithiocarbamates which, in particular, yields zinc dithiocarbamates in readily filterable form, that is to say with a large particle size and a distribution of the re-suiting particle sizes that is as uniform as possible.

Accordingly, the invention provides a process for the preparation of zinc dithiocarbamates of the formula

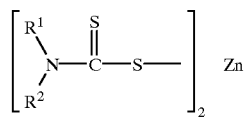

wherein $R^1$ and $R^2$ are identical or different, preferably identical, and represent $C_1$–$C_6$-alkyl or $C_7$–$C_{12}$-aralkyl radicals, or wherein $R^1$ and $R^2$ are bridged by polymethylene chains having from 2 to 12 methylene segments, it being possible for the polymethylene chains to be interrupted by from 1 to 3 hetero atoms, such as oxygen, sulfur or nitrogen, wherein the process is characterized in that zinc salts are first added, in aqueous solution, to the secondary amines underlying the zinc carbamates, so that a zinc salt complex of the amines is formed, and carbon disulfide and sodium hydroxide solution are then introduced, with stirring, into the aqueous suspension so obtained, the temperatures being maintained at from room temperature (approximately 20° C.) to the boiling temperature of carbon disulfide (42° C. at normal pressure) until the reaction has completely finished.

The process according to the invention can be illustrated using the example of the preparation of zinc dibenzyldithiocarbamate by the following reaction scheme:

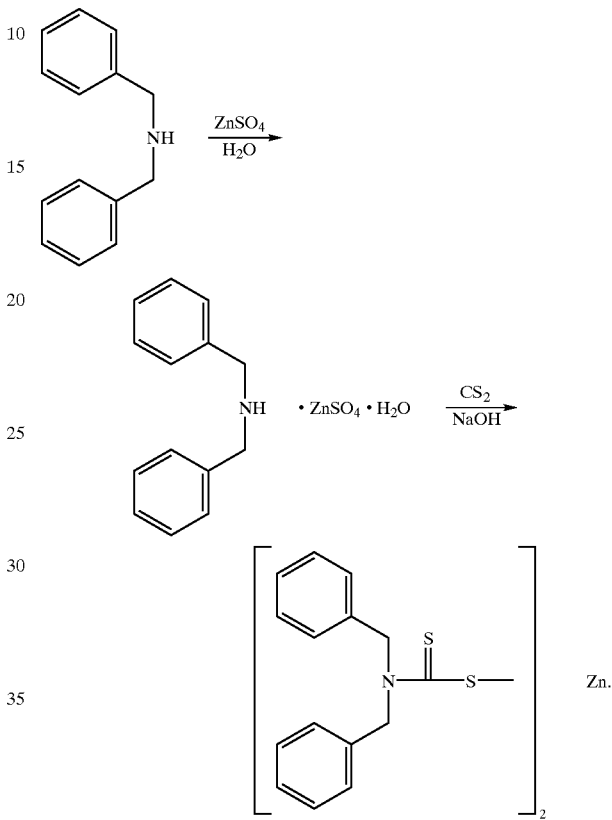

Suitable secondary amines that can be used for the preparation of the dithiocarbamates are, for example: dimethylamine, diethylamine, dipropylamine, dibutylamine, piperidine, morpholine, N-methylpiperazine, N-ethylpiperazine, dibenzylamine, diarylamine, ethylaniline, methylaniline, methyl-tert.-butylamine and ethyl-tert.-butylamine.

Dibenzylamine, dimethylamine, diethylamine, dibutylamine, piperidine and morpholine are preferred, and dibenzylamine is most preferred.

Examples of zinc salts that are reacted according to the present invention with the secondary amines in aqueous solution, preferably under an inert gas atmosphere (e.g. nitrogen), are: zinc sulfate, zinc chloride and/or zinc acetate, in particular zinc sulfate.

The zinc salts are preferably reacted with the secondary amines in from 1 to 25% aqueous solution, the zinc salts being used in a ratio of from (0.8 to 1.2):1, preferably 1:1, relative to the secondary amines.

The zinc salt complexes of the secondary amines so obtained are then reacted with carbon disulfide, the amount of carbon disulfide used being from a slight excess up to a maximum of 5 wt. %, based on the amount of zinc salt complexes of the secondary amines.

The reaction of the zinc salt complexes of the secondary amines with carbon disulfide takes place with vigorous stirring, the suspension preferably being maintained at from 30 to 40° C.

With the addition of lye, preferably sodium hydroxide solution (from 5 to 10% strength), stirring is carried out, at the temperature indicated, until the reaction has completely finished. The sodium hydroxide solution is normally employed in a stoichiometric amount. A slight excess of up to approximately 5 wt. % is possible.

The resulting zinc dithiocarbamate is then filtered, washed, for example with water and/or with isopropanol, and then dried, advantageously in vacuo.

The zinc dithiocarbamates are obtained by the process according to the present invention with average primary particle sizes, which are a multiple of the normal size, the particle-size distribution being very homogeneous. In the case of zinc dibenzyldithiocarbamate, the primary particle size obtained according to the present invention is approximately $100\mu$ instead of $5\mu$ as in the synthesis method employed hitherto, as will be seen with reference to the SEM image. The yields by the process according to the present invention can reach over 99% of the theoretical yield. In general, they are from 98 to 99%.

In the process according to the present invention, it has proven advantageous, particularly in the case of longer-chained amines, to carry out the reaction of the secondary amines in aqueous solution with the zinc salts in the presence of an emulsifier, such as Emulgator® L3 from Bayer AG. The amount of emulsifier is approximately from 0.1 to 0.5 wt. %, based on secondary amine used, but preferably from 0.2 to 0.3 wt. %.

EXAMPLES

Example 1
Preparation of Zinc Dibenzyldithiocarbamate
Preparation

To 788 g of dibenzylamine, 2 g of Emulgator® L3 (Bayer AG) and 800 g of water there is added dropwise under nitrogen, in the course of 16 minutes, a solution of 575 g of zinc sulfate (containing 7 mol of water of crystallization) and 3200 g of water at 20 to 21° C., with vigorous stirring (10 liter flask).

A white, coarsely crystalline precipitate forms which, according to analysis, is a dibenzylamine adduct on zinc sulfate containing 3 mol of water of crystallization. 314 g of carbon disulfide are introduced dropwise into that suspension, beneath the surface of the suspension, in the course of one hour, by means of a dropping funnel provided with an elongate spout. During the introduction, the temperature rises from 21 to 24° C. The mixture is then heated to 35° C. in the course of 38 minutes. A solution of 160.2 g of sodium hydroxide and 2000 g of water is then added dropwise, with continued heating, in the course of 40 minutes, whereupon the temperature rises to 40° C. Stirring is carried out for 70 minutes at 40° C., and the mixture is then filtered off with suction, while warm, and washed several times with water having a temperature of 80° C. The product can be filtered off with suction very readily, within a few minutes. Drying is then carried out in vacuo at 50° C. over sodium hydroxide. 1203 g of an almost white zinc dibenzyldithiocarbamate having a melting point of from 185 to 187° C. are obtained. The yield is 98.9% of the theoretical yield.

The particle size of the crystallites is on average approximately $100\mu$ according to the SEM image.

Example 2 (Comparison)

788 g of dibenzylamine are stirred at 10° C. in 2 liters of water and 160 g of sodium hydroxide solution. In the course of 2.5 hours, 304.5 g of carbon disulfide are added. During the addition, the mixture warms to 30° C. in the course of 30 minutes.

At that temperature, stirring is continued for a further 4 hours after the addition of the carbon disulfide.

3 liters of water are then added, and 273.5 g of $ZnCl_2$ (dissolved in 1 liter of water) are added at 40° C. in the course of 2 hours, and stirring is then carried out for from 3 to 4 hours.

Filtering off of the pasty mixture with suction takes several hours.

The primary particle size of the resulting carbamate is approximately from 2 to $3\mu$ on average.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:
1. A process for the preparation of zinc dithiocarbamates of the formula

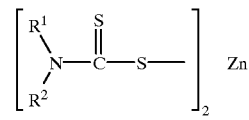

wherein
$R^1$ and $R^2$ are identical or different and represent a $C_1$–$C_6$-alkyl or $C_7$–$C_{12}$-aralkyl radical,
or wherein
$R^1$ and $R^2$ are bridged by polymethylene chains having from 2 to 12 methylene segments, it being possible for the polymethylene chains to be interrupted by from 1 to 3 hetero atoms,
wherein said process comprises the following steps in sequence of: (i) adding zinc salts, in aqueous solution, to secondary amines underlying the zinc carbamates, (ii) forming an aqueous suspension of zinc salt complex of the secondary amines, and (iii) introducing carbon disulfide and sodium hydroxide solution, with stirring, into said aqueous suspension, whereby the temperatures are maintained in the range from room temperature to the boiling temperature of carbon disulfide until the reaction has completely finished and wherein said zinc dithiocarbamates have a homogeneous particle size distribution.

2. A process according to claim 1, wherein the molar ratio of zinc salts to secondary amines is from (0.8 to 1.2):1.

3. A process according to claim 1, wherein the temperature range maintained is from 30 to 40° C.

* * * * *